United States Patent [19]

Sorensen

[11] Patent Number: 4,890,625
[45] Date of Patent: Jan. 2, 1990

[54] BLOOD PRESSURE CUFF WITH INTEGRAL ACOUSTIC PICKUP CUP

[75] Inventor: Jay R. Sorensen, Aloha, Oreg.

[73] Assignee: SpaceLabs, Inc., Bothell, Wash.

[21] Appl. No.: 172,718

[22] Filed: Mar. 24, 1988

[51] Int. Cl.⁴ ............................................. A61B 5/02
[52] U.S. Cl. ................................. 128/680; 128/686; 128/715
[58] Field of Search .................. 128/672, 677–686, 128/715

[56] References Cited

U.S. PATENT DOCUMENTS

| | | | |
|---|---|---|---|
| 3,555,187 | 1/1971 | Rowley | 128/715 |
| 3,621,831 | 11/1971 | Pisacano | 128/686 |
| 3,757,772 | 9/1973 | Goldblat et al. | 128/686 |
| 3,905,354 | 9/1975 | Lichowsky | 128/681 |
| 3,935,984 | 2/1976 | Lichowsky et al. | 128/686 |
| 4,141,350 | 2/1979 | Shinoda | 128/680 |
| 4,214,589 | 7/1980 | Sakamoto et al. | 128/680 |
| 4,337,778 | 7/1982 | Akira et al. | 128/680 |
| 4,729,382 | 3/1988 | Schaffer et al. | 128/681 |

Primary Examiner—Angela D. Sykes
Attorney, Agent, or Firm—Seed and Berry

[57] ABSTRACT

A blood pressure cuff having an internal acoustic pickup cup. In one embodiment, the cup communicates with the interior of the blood pressure cuff bladder through an aperture that is sufficiently large to allow pressure equalization between the interior of the bladder and the cup and sufficiently small to prevent Karotkoff sounds from being coupled from the cup to the interior of the bladder. A single pneumatic tube extends from the cup and through the wall of the bladder to a first enclosure that is coupled to a second enclosure through a conduit. The first enclosure contains a microphone for converting the acoustic signals picked up by the cup into a corresponding electrical signal. The second enclosure contains a pressure transducer for providing an electrical signal indicative of the pressure in the bladder. In a second embodiment, the cup and bladder are isolated from each other and separate tubes extend from the bladder and the cup to separate enclosures. The enclosure communicating through one of the conduits with the cup contains a microphone, while the enclosure communicating through the other tube with the bladder contains a pressure transducer.

12 Claims, 1 Drawing Sheet

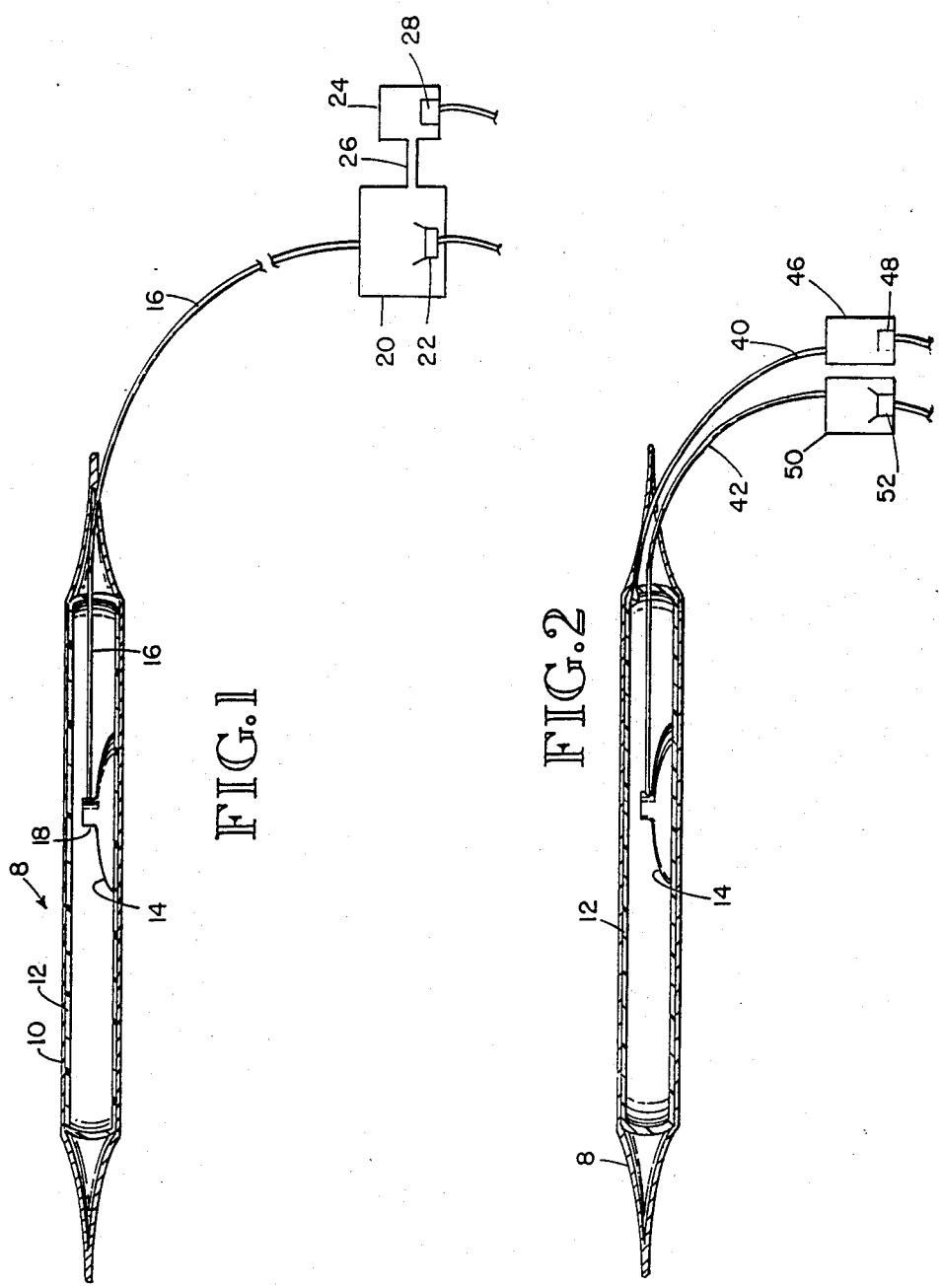

BLOOD PRESSURE CUFF WITH INTEGRAL ACOUSTIC PICKUP CUP

FIELD OF THE INVENTION

This invention relates to blood pressure monitoring, and more particularly, to a blood pressure cuff having a built-in acoustic pickup cuff for detecting acoustic signals generated by blood flow in arteries beneath the cuff.

BACKGROUND ART

Blood pressure is normally measured by placing a blood pressure cuff around the arm of a patient over the brachial artery. The cuff typically includes an inflatable bladder placed in an outer casing. The bladder is inflated to compress the arm of the patient, thereby pinching off the flow of blood through the brachial artery. The pressure in the bladder is gradually reduced while listening for sounds caused by the flow of blood through the brachial artery and measuring the air pressure in the bladder. When blood flow is detected during systole, the air pressure in the bladder is recorded as the systolic blood pressure. Similarly, when blood flow is detected during diastole, the air pressure in the bladder is recorded as the diastolic blood pressure.

The most common device for measuring blood pressure using the above-described procedure is the familiar manually pumped cuff using a mercury manometer as the pressure measuring device. After the cuff is inflated with air, the pressure in the cuff is gradually reduced while a stethoscope is used to detect the flow of blood in the brachial artery beneath the cuff.

Automated patient monitoring systems are also in common use to allow blood pressure measurements to be periodically taken without the assistance of medical personnel. In these automated systems, a blood pressure cuff is periodically inflated and the blood pressure is then gradually reduced while the cuff pressure is measured. An electrical or acoustic audio pickup device listens for the sound generated as blood starts flowing through the brachial artery to determine the systolic and diastolic blood pressures.

One conventional automated blood pressure monitor utilizes a miniature microphone built into the blood pressure cuff to detect the flow of blood. However, the use of a microphone in the blood pressure cuff has several disadvantages. The microphones, being somewhat fragile, are susceptible to breakage, particularly in heavy clinical use. It is also difficult to maintain the sterility of blood pressure cuffs having built-in microphones. They cannot be sterilized because the heat and moisture of typical autoclaves would destroy the microphone. The common alternative to sterilization in the medical field of making devices disposable after a single use is precluded by the relatively high expense of blood pressure cuffs having build-in microphones. Thus, there is no convenient method of sterilizing blood pressure cuffs having internal microphones. The signal-to-noise ratio of microphones installed in blood pressure cuffs in also limited by the noise picked up in the relatively long leads extending from the cuff to a monitor. Finally, the microphones, being electrical devices, require that the blood pressure cuffs be electrically isolated from patients.

Another approach to combining the blood pressure cuff with a device for detecting blood flow sounds is to use the blood pressure cuff itself as the acoustic pickup device. The pulsating nature of arterial blood flow produces pressure waves that are reflected as pressure variations in the bladder of the cuff. These pressure variations are coupled through a tube conected to the cuff to a pressure transducer where the pressure variations are converted to electrical signals. The use of the bladder as the pickup device has the advantages that it is relatively inexpensive, so it can be disposed of after a single use, and it is very sturdy, so it can be sterilized and can withstand heavy use without damage. Further, because it has no electrical components, electrical isolation from the patient is not required. However, this approach has a major performance limitation because it is capable of picking up only low-frequency blood flow sounds. The pressure waves generated by blood flowing through the brachial artery consist of oscillatory pressure waves having frequency components in the 1 to 6 Hz range and Korotkoff sounds having frequency components in the 18 to 250 Hz range.

It is commonly believed that the auscultatory method of blood pressure monitoring, in which the Korotkoff sounds are used to detect blood flow, is more advantageous than using the oscillatory pressure waves for that purpose. However, a blood pressure cuff bladder is only capable of picking up oscillatory pressure waves; it is not capable of picking up Korotkoff sounds. Basically, the relatively large-volume bladder functions like the electrical equivalent of a capacitor. Just as a capacitor has the tendency to filter or average high-frequency electrical signals, the bladder filters or averages high-frequency acoustic signals so that the high-frequency acoustic signals are not coupled down the tube connected to the bladder. The use of the blood pressure bladder as an acoustic pickup device also has the disadvantage of picking up a great deal of extraneous low-frequency noise that is present in most patient monitoring environments.

DISCLOSURE OF THE INVENTION

It is an object of the invention to provide a combination blood pressure cuff and acoustic pickup device that is capable of picking up Korotkoff sounds as well as oscillatory pressure waves.

It is another object of the invention to provide a combination blood pressure cuff and acoustic pickup device for detecting blood flow that is sturdy enough to withstand heavy usage and be repeatedly sterilized.

It is still another object of the invention to provide a combination blood pressure cuff and acoustic pickup device for detecting blood flow that is inexpensive enough to be discarded after a single use.

It is a further object of the invention to provide a combination blood pressure cuff and acoustic pickup device for detecting blood flow that has no electrical interface so that it need not be electrically isolated from a patient being monitored.

These and other objects of the invention are provided by a blood pressure cuff including a flexible casing having a rectangular pocket, a relatively thin, flexible rectangular bladder positioned in the pocket, and an acoustic pickup cup mounted in the bladder in a manner that allows the cup to pick up Korotkoff sounds when the blood pressure cuff is placed on a patient.

In one embodiment, a single pneumatic tube extends from the interior of the cup through the envelope to either a single enclosure containing a pressure transducer or one of two interconnected enclosures, one of which contains a microphone and the other of which contains a pressure transducer. In this embodiment, an aperture is formed in the cap to allow the pressure in the interior of the bladder and the pressure in the interior of the cup to equalize. As a result, the pressure in said bladder and the acoustic signals picked up by the cup are both coupled through the tube to the enclosure(s).

In a second embodiment, a first pneumatic tube extends from the interior of the bladder to an enclosure containing a pressure transducer, and a second pneumatic tube extends from the interior of the cup through the bladder to an enclosure containing a microphone.

BRIEF DESCRIPTION OF THE DRAWINGS

FIG. 1 is a schematic of one embodiment of a combination bloodo pressure cuff and acoustic pickup device for detecting blood flow.

FIG. 2 is a schematic of another embodiment of a combination blood pressure cuff and acoustic pickup device for detecting blood flow.

BEST MODE FOR CARRYING OUT THE INVENTION

One embodiment of the blood pressure cuff 8 having an integral acoustic pickup cup is illusrated in FIG. 1. The cuff 8 utilizes a conventional casing 10, enclosing a resilient bladder 12. The bladder 12 has the same relatively thin, elongated rectangular configuration of conventional blood pressure bladders. However, the bladder 12 also includes a circular cup 14 attached to the inner wall of the bladder. The cup 14 preferably has a circular configuration, but other shapes, such as oval, rectangular, etc., may also be used. The size of the cup 14 is not critical, but it should be sufficiently small that it will not have a tendency to average Korotkoff sounds in the frequency range of 18 to 250 Hz. A cup 14 having a diameter of about 1 inch is preferred. A pneumatic tube 16 extends from the cup 14 and through the bladder 12. The bladder 12 is sealed to the tube 16 so that the bladder 12 is entirely enclosed except for a small aperture 18 between the interior of the bladder 12 and the interior of the cup 14. The aperture 18 allows pressure equalization between the interior of the bladder 12 and the interior of the cup 14. THe size of the aperture should be sufficiently small that it will not readily pass high-frequency sounds but large enough that it can allow fast equalization between the pressure in the bladder 12 and the pressure in the cup 14, particularly as the bladder 12 is inflated through the tube 16. An aperture having a diameter of about 0.1 inch is preferred.

The pneumatic tube 16 extending from the bladder 12 is connected to a first enclosure 20 having a microphone 22 mounted therein. A second enclosure 24 connected to the first enclosure 20 through a conduit 26 has a conventional pressure transducer 28 mounted therein.

In operation, the bladder 12 is placed in the blood pressure cuff casing 10, and the casing 10 is then snugly wrapped around the arm of a patient over the patient's brachial artery. The bladder 12 is then inflated, either manually or by an air pump in an automatic blood pressure monitor. After the bladder 12 has been inflated to a predetermined pressure, it is vented through the tube 16 so that its pressure decreases, either gradually or in increments. The aperture 18 between the interior of the bladder 12 and the interior of the cup 14 allows prompt equalization between the pressures in the bladder 12 and the cup 14. As a result,t he pressure in the tube 16 is the same as the pressure in the bladder 12. The pressure in the tube 16 is coupled to the enclosure 24 through the enclosure 20 and the conduit 26, and this pressure is measured by the pressure transducer 28. At the same time, the Korotkoff sounds are picked up by the cup 14. The relatively small size of the aperture 18 prevents these sounds from being coupled to the interior of the bladder 12 so that they are not thereby attenuated. Instead, the Korotkoff sounds are coupled through the tube 16 to the enclosure, where the acoustic signal in the tube 16 to the enclosure, where the acoustic signal in the tube 16 is converted to a corresponding electrical signal by the microphone 22.

Although the embodiment of FIG. 1 is illustrated as using separate enclosures 20, 24 for the microphone 22 and pressure transducer 28, it will be understood that the microphone 22 and pressure transducer 28 may be placed together in a single enclosure. In this case, a separate microphone 22 and transducer 28 may not be required since a single pressure transducer may be used as long as it responds to pressure variations in the 18 to 250 Hz frequency range as well as steady-state pressure.

Another embodiment of a blood pressure cuff having an integral acoustic pickup cup is illustrated in FIG. 2. The embodiment of FIG. 2 differs from the embodiment of FIG. 1 by using separate pneumatic tubes 40, 42 for the bladder 12 and the cup 14, respectively. As a result, the cup 14 does not require an aperture between the cup 14 and the interior of the bladder 12 since there is no need for pressure equalization. In fact, the cup 14 may be open to atmospheric pressure, as illustrated in FIG. 2. The tube 40 extending from the bladder 12 communicates with the interior of a housing 46 containing a conventional pressure transducer 48 that provides an electrical indication of the pressure in the bladder 12. Similarly, the tube 42 extending from the cup 14 communicates with the interior of a separate housing 50 containing a microphone 52 that converts the acoustic signals detected by the cup 14 into corresponding electrical signals.

Although the embodiment illustrated in FIG. 2 uses a cup 14 that is open to atmospheric pressure, it will be understood that the cup 14 may be isolated from the atmosphere and communicate with the interior of the bladder 12. If the pressure of the cup 14 is not equalized with the pressure in the bladder 12, the cup 14 should be fairly rigid so that it will not be collapsed excessively by the greater pressure in the bladder 12.

The inventive blood pressure cuff thus combines a blood pressure cuff with an acoustic pickup device in a manner that makes the cuff sturdy and inexpensive. Furthermore, the cuff does not require electrical isolation between the cuff and a blood pressure monitor, and the acoustic pickup is capable of detecting the relatively high-frequency Korotkoff sounds.

I claim:

1. A blood pressure cuff comprising:
   a flexible casing having a rectangular pocket formed therein;
   a relatively thin, flexible rectangular bladder positioned in the pocket of said casing;
   an acoustic pickup cup mounted in said bladder in a manner that allow said cup to pick up Korotkoff sounds when said blood pressure cuff is placed on a patient, said cup having an aperture formed therein between the interior of said cup and the interior of said bladder to allow the pressure in the interior of said cup to equalize; and a pneumatic tube extending from the interior of said cup through said bladder, whereby the pressure in said bladder and acoustic signals picked up by said cup are both coupled through said tube.

2. The blood pressure cuff of claim 1 wherein said aperture has a diameter of about 0.1 inch.

3. A system for measuring blood pressure, comprising:
a blood pressure cuff including a flexible casing having a rectangular pocket formed therein, a flexible rectangular bladder positioned in the pocket of said casing, and an acoustic pickup cup to pick up Korotkoff sounds when said blood pressure cuff is placed on a patient, said cup having an aperture formed therein between the interior of said cup and the interior of said bladder to equalize the pressure in said bladder with the pressure in said cup;
an enclosure having a pressure transducer generating an electrical signal indicative of the pressure in said enclosure and an electrical signal corresponding to an acoustic signal coupled to said enclosure; and
a pneumatic tube extending from the interior of said acoustic pickup cup through said bladder to said enclosure for coupling the pressure in said bladder and acoustic signals picked up by said cup into the interior of said enclosure.

4. The blood pressure measuring system of claim 3 wherein said pressure transducer comprises a microphone generating said electrical signal corresponding to said acoustic signal; and
pressure transducer means generating said signal indicative of the pressure in said enclosure.

5. The blood pressure measuring system of claim 4 wherein said microphone and said pressure transducer means are mounted in separate respective first and second enclosures that are coupled to each other.

6. The blood pressure measuring system of claim 5 wherein said penumatic tube means comprise a first pneumatic tube extending from the interior of said cup through said bladder to said first enclosure and a second pneumatic tube extending from the interior of said bladder to said second enclosure.

7. The blood pressure measuring system of claim 6 wherein said acoustic pickup cup is open to the atmosphere and wherein said acoustic pickup cup has sufficient rigidity to withstand the pressure differential across said cup when said bladder is inflated.

8. The blood pressure measuring system of claim 3 wherein said aperture has a diameter of about 0.1 inch.

9. A method of measuring blood pressure, comprising:
providing a blood pressure cuff having a flexible casing with a rectangular pocket formed therein, a flexible rectangular bladder positioned in the pocket of said casing, and an acoustic pickup cup mounted in said bladder in a manner that allows said pickup cup to pick up Korotkoff sounds when said blood pressure cuff is placed on a patient;
placing said blood pressure cuff around the limb of a patient and selectively inflating or deflating said bladder so that Korotkoff sounds generate relatively high-frequency pressure signals in said pickup cup;
venting the interior of said pickup cup to the interior of said bladder so that the pressure in said cup and the pressure in said bladder are substantially equalized; and
measuring the pressure in said pickup cup to both detect Korotkoff sound-induced pressure signals in said pickup cup and determine the fluid pressure in said bladder.

10. The method of claim 9 wherein the pressure in said pickup cup is measured by connecting the interior of said pickup cup to a pressure transducer with a pneumatic tube extending from the interior of said acoustic pickup cup through said bladder and to said pressure transducer without allowing said pneumatic tube to communicate directly with the interior of said bladder.

11. The method of claim 9 wherein said acoustic pickup cup is mounted within said bladder, and further comprising forming an aperture in said acoustic pickup cup between the interior of said acoustic pickup cup and the interior of said bladder to vent the interior of the acoustic pickup cup to the interior of the bladder, said aperture having a diameter that is sufficiently small to substantially prevent Korotkoff sound-induced pressure signals in said pickup cup from being coupled to the interior of said bladder.

12. The method of claim 11 wherein the diameter of said aperture is about 0.1 inch.

* * * * *

UNITED STATES PATENT AND TRADEMARK OFFICE
CERTIFICATE OF CORRECTION

PATENT NO. : 4,890,625

DATED : January 2, 1990

INVENTOR(S) : Jay R. Sorensen

It is certified that error appears in the above-identified patent and that said Letters Patent is hereby corrected as shown below:

On the cover page, delete "Assignee: SpaceLabs, Inc., Bothell Wash." and substitute therefor --Assignee: SpaceLabs, Inc., Redmond, Wash.--.

Signed and Sealed this

Fourteenth Day of January, 1992

Attest:

HARRY F. MANBECK, JR.

*Attesting Officer*  *Commissioner of Patents and Trademarks*